US007286942B1

(12) United States Patent
Kish et al.

(10) Patent No.: US 7,286,942 B1
(45) Date of Patent: Oct. 23, 2007

(54) SYSTEM AND METHOD OF FLUCTUATION ENHANCED GAS-SENSING USING SAW DEVICES

(75) Inventors: Laszlo B. Kish, College Station, TX (US); Gabor Schmera, San Diego, CA (US)

(73) Assignee: United States of America as Represented By The Secretary of the Navy, Washington, DC (US)

( * ) Notice: Subject to any disclaimer, the term of this patent is extended or adjusted under 35 U.S.C. 154(b) by 832 days.

(21) Appl. No.: 10/677,684

(22) Filed: Oct. 2, 2003

Related U.S. Application Data

(60) Provisional application No. 60/475,058, filed on May 30, 2003.

(51) Int. Cl.
- *G01N 31/00* (2006.01)
- *G01N 19/00* (2006.01)
- *B32B 5/02* (2006.01)
- *B32B 27/04* (2006.01)
- *B32B 27/12* (2006.01)

(52) U.S. Cl. .............................. 702/22; 422/50; 422/62; 422/67; 422/68.1; 422/82.01; 422/83; 422/98; 73/1.01; 73/1.02; 436/43; 436/149; 700/1; 700/266; 702/1; 702/19; 702/23; 702/30; 702/31; 702/32; 702/57 G

(58) Field of Classification Search .................. 422/50, 422/62, 67, 68.1, 82.01, 83, 98; 73/1.01, 73/1.02; 436/43, 149; 700/1, 266; 702/1, 702/19, 22, 30, 31, 32, 57, 23
See application file for complete search history.

(56) References Cited

U.S. PATENT DOCUMENTS

| 4,638,443 A | 1/1987 | Kaneyasu |
| 4,895,017 A | 1/1990 | Pyke |
| 5,076,094 A | 12/1991 | Frye |

(Continued)

FOREIGN PATENT DOCUMENTS

WO    WO 83/01511    4/1983

OTHER PUBLICATIONS

G. Watson, et. al, "Gas Chromatography Utilizing SAW Sensors", 1991 Ultrasonics Symposium, 5 pages, Westlake Village, CA 91361.

(Continued)

*Primary Examiner*—Brian Sines
(74) *Attorney, Agent, or Firm*—Pete A. Lipovsky; Allan Y. Lee; Ryan J. Friedl

(57) ABSTRACT

A system and method of fluctuation enhanced gas-sensing using SAW devices includes processes for improved chemical analyte detection, identification, and quantification through the measurement and spectral analysis of frequency fluctuations in the instantaneous frequency of a chemical sensor arranged to produce an oscillatory output signal when exposed to chemical substances. The system and method may use a chemical sensor, such as a surface acoustic wave (SAW) device. The spectral analysis produces the power spectral density of the frequency fluctuations, which are represented as a pattern that includes information about the analyte(s) such as, total adsorbed gas mass and diffusion coefficients. The diffusion coefficients may then be used to determine the number of molecule types and/or the concentration of each.

20 Claims, 5 Drawing Sheets

U.S. PATENT DOCUMENTS

| | | | |
|---|---|---|---|
| 5,117,146 | A | 5/1992 | Martin |
| 5,411,709 | A | 5/1995 | Furuki |
| 5,469,369 | A | 11/1995 | Rose-Pehrsson |
| 5,885,844 | A | 3/1999 | Weir |
| 6,044,332 | A | 3/2000 | Korsah |
| 6,170,318 | B1 | 1/2001 | Lewis |
| 6,293,136 | B1 | 9/2001 | Kim |
| 6,350,369 | B1 | 2/2002 | Lewis et al. |
| 6,360,585 | B1 | 3/2002 | Potyrailo et al. |
| 6,387,329 | B1 | 5/2002 | Lewis et al. |
| 7,122,152 | B2 * | 10/2006 | Lewis et al. .................. 422/50 |

OTHER PUBLICATIONS

Gardner, Julian, et al, "Performance Definition and Standardisation of Electronic Noses", Transducers '95—Eurosensors IX, Jun. 1995, 4 pages, 8th Internat'l Conference. . . .

Hines, E.L., et al, "Electronic Noses: a Review of Signal Processing Techniques", IEE Proc.—Circuits Devices Syst., vol. 146, No. 6, Dec. 1999, 14 pages.

Craven, M.A., et al, "Electronic Noses—Development and Future Prospects", Trends in Analytical Chemistry, vol. 15, No. 9, 1996, 8 pages, Elsevier Science B.V.

Wide, Peter, et. al, "The Human-bases Multi-sensor Fusion Method for Artificial Nose. . .", IEEE Instrumentation and Measurement Technology Conference, May 1998, 6 pages.

Bryant, A., et. al, "A Surface Acoustic Wave Gas Detector", 36th Annual Frequency Control Symposium, 1982, 8 pages.

Watson, G., et. al, "SAW Resonators as Vapor Sensors", Ultrasonics Symposium, 1990, 4 pages.

Vig, John R., et. al, "Noise in Microelectromechanical System Resonators", IEEE Transactions on ultrasonics. . ., vol. 46, No. 6, Nov. 1999, 8 pages.

MacFarlane, G. G., "A Theory of Contact Noise in Semiconductors", Proc. Phys. Soc, 1950, 8 pages.

Burgess, R.E., "Contact Noise in Semiconductors", Proc. Phys. Soc, 1953, 2 pages.

Weissman, M.B., "1/f Noise and Other Slow, NonExponential Kinetics in Condensed Matter", Reviews of Modern Physics, vol. 60, No. 2, Apr. 1988, 35 pages, American Physical Soc.

* cited by examiner

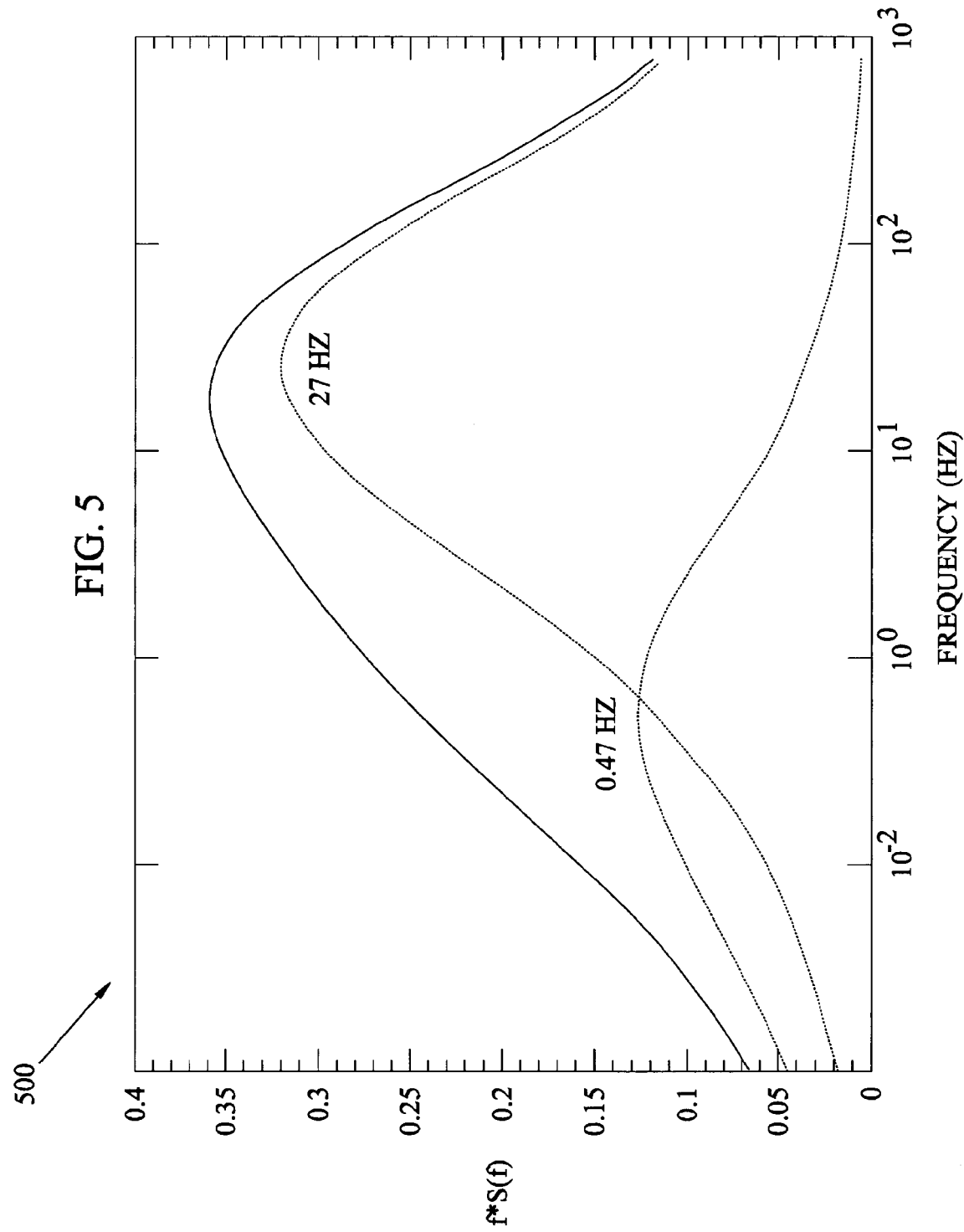

SYSTEM AND METHOD OF FLUCTUATION ENHANCED GAS-SENSING USING SAW DEVICES

CROSS-REFERENCE TO RELATED APPLICATIONS

This application claims the benefit of U.S. Provisional Application No. 60/475,058, filed May 30, 2003, herein incorporated by reference.

FEDERALLY-SPONSORED RESEARCH AND DEVELOPMENT

The system and method of fluctuation enhanced gas-sensing using SAW devices is assigned to the United States Government and is available for licensing for commercial purposes. Licensing and technical inquiries should be directed to the Office of Patent Counsel, Space and Naval Warfare Systems Center, San Diego, Code 20012, San Diego, Calif., 92152; telephone (619)553-3001, facsimile (619)553-3821.

BACKGROUND

The system and method of fluctuation enhanced gas-sensing using SAW devices generally relates to chemical analyte detection and identification, and more particularly, to a system and method of chemical analyte detection and identification by analysis of frequency fluctuations in a chemical sensor arranged to produce an oscillatory output signal when exposed to chemical substances.

Homeland defense, including anti-terrorist efforts require highly selective, sensitive, and reliable detection of harmful agents. Intensive research has resulted in the use of chemical and biological sensor elements for the development of systems known as electronic noses (for gas and odor sensing) and electronic tongues (for fluid sensing).

Presently available electronic noses and tongues are most commonly based on the measurement of conductance or the electrochemical potential of surface-active devices. Such noses and tongues are not sufficiently reliable, selective, nor sensitive for certain applications. In addition, these sensor components have high false alarm rates and short lifetimes.

A more sensitive and reliable way of gas sensing is based on surface acoustic wave (SAW) devices. These devices generally operate by measuring the propagation velocity of acoustic waves between electrode pairs. As gas molecules are adsorbed by the SAW device the mass of the SAW device is increased, thereby reducing the propagation velocity between the electrode pairs. Traditionally, only the average resonant frequency of the propagating wave is measured and microfluctuations of the instantaneous frequency are ignored. This method of only measuring average resonant frequency is not selective (only the adsorbed mass is measured) and is highly susceptible to inaccuracies due to changes in temperature.

Therefore, it can be appreciated that a highly selective, sensitive, and reliable method of gas-sensing that is less susceptible to inaccuracies due to changes in temperature is needed.

SUMMARY

The present invention provides a system and method of fluctuation enhanced gas-sensing using SAW devices that address the problems mentioned previously.

In one aspect of the invention, a method for analyzing a chemical analyte includes the steps of: (1) generating a fluctuation output signal in response to a plurality of frequency fluctuations in the oscillatory output signal of a surface acoustic wave device; (2) transforming the fluctuation output signal into a power spectral density signal that represents the power spectral density of the frequency fluctuations; (3) generating a diffusion coefficient signal that represents a diffusion coefficient of the analyte; and (4) generating an analyte output signal that is representative of a characteristic of the analyte in response to the diffusion coefficient signal.

In another aspect of the invention, a chemical sensor system is provided that includes a chemical sensor arranged to produce an oscillatory output signal when exposed to a chemical analyte. The chemical sensor system also includes: measurement means for measuring a plurality of frequency fluctuations of the oscillatory output signal of the sensor; PSD means for generating a spectral density signal representative of the power spectral density of the frequency fluctuations; diffusion coefficient means for generating a diffusion coefficient signal representative of a diffusion coefficient of the chemical analyte; and decision means for generating an analyte output signal representative of a characteristic of the analyte in response to the diffusion coefficient signal.

In still another aspect of the invention a computer program product (CPP) is provided that includes a machine-readable recording medium and a first, second, third, and fourth instruction means recorded on the medium for use with a chemical sensor system that includes a chemical sensor arranged to produce an oscillatory output signal when exposed to a chemical analyte. The first, second, third, and fourth instruction means are recorded on the medium for directing the chemical sensor system to: (1) generate a fluctuation output signal in response to a plurality of frequency fluctuations in the oscillatory output signal of the chemical sensor; (2) generate a power spectral density signal representative of the power spectral density of the frequency fluctuations; (3) generate a diffusion coefficient signal representative of a diffusion coefficient of the chemical analyte; and (4) generate an analyte output signal representative of a characteristic of the analyte in response to the diffusion coefficient signal.

BRIEF DESCRIPTION OF THE DRAWINGS

FIG. 5 is a view showing the f*S(f) pattern for a SAW device measuring two chemical agents in accordance with the system and method of fluctuation enhanced gas-sensing using SAW devices.

DESCRIPTION OF SOME EMBODIMENTS

Following is a glossary of terms used to describe the system and method of fluctuation enhanced gas-sensing using SAW devices. The definitions set forth in the glossary are representative of the intended meanings as used herein.

Glossary

The term "bandpass filter" means a wave filter that attenuates frequencies on one or both sides of a single transmission band.

The term "chemical analyte" means a substance being measured in an analytical procedure.

The term "chemical sensor" means a device that responds to chemical stimulus.

The term "diffusion coefficient" means a coefficient used to represent the random motion of the molecules on the surface of the SAW device. By way of example, the diffusion coefficient may be represented by: $\langle r^2 \rangle \propto D \cdot t$, where r is the distance traveled by an analyte molecule, D is the diffusion coefficient, t is elapsed time, and where the angle brackets represent the arithmetic mean operation.

The term "frequency counter" means an instrument in which frequency is measured by counting the number of cycles occurring during an established time interval.

The term "machine-readable recording medium" means a physical material in or on which data may be represented wherein the data can be read by an input unit for storage, processing, or display.

The term "power spectral density" means the power distribution of a signal with respect to frequency.

Figure 1:
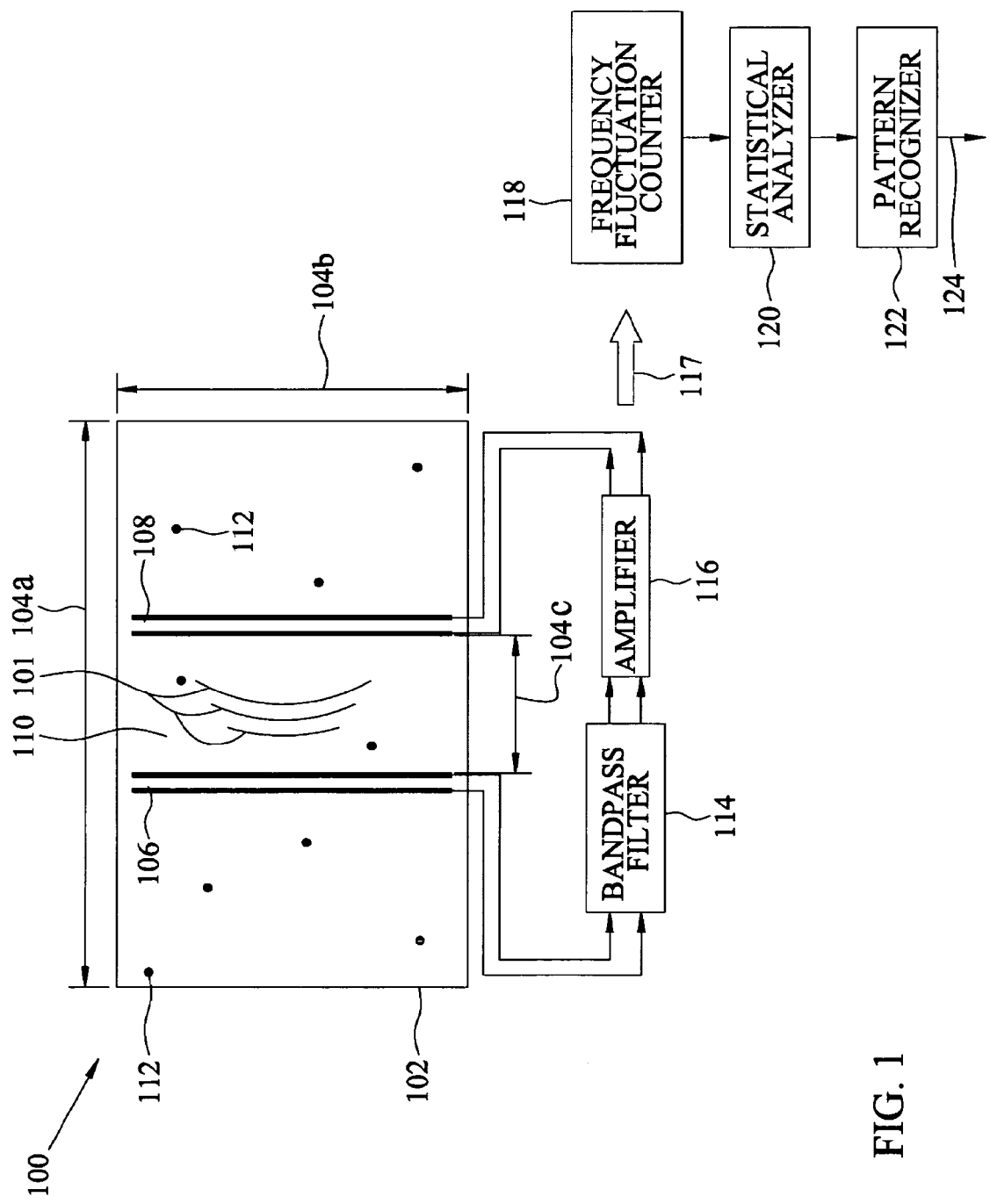
FIG. 1 is a block diagram of a chemical sensor system in accordance with the system and method of fluctuation enhanced gas-sensing using SAW devices.

FIG. 1 shows a block diagram of a gas-sensing SAW device 102 in an chemical sensor system 100, in accordance with the system and method of fluctuation enhanced gas sensing using SAW devices. SAW device 102 typically includes two electrode pairs 106 and 108. Although SAW device 102 is shown in FIG. 1 as only having two electrodes, it is recognized that any number of electrode pairs for the generation and measurement of surface propagating waves on a SAW device may be implemented. The space between electrode pairs 106 and 108 is referred to as the gas-sensing region 110 or the "sweetspot". In operation, the extra inertial mass of adsorbed molecules 112 decreases the propagation velocity of a generated surface acoustic wave 101 and thus the delay time increases between electrode pairs 106 and 108. The propagation velocity of surface acoustic wave 101 is approximately proportional to the number of adsorbed molecules 112 in the gas-sensing region 110.

The gas molecules 112 adsorbed on the surface of SAW device 102 execute a surface diffusion process, which is essentially a random walk over the entire surface of SAW device 102. Assuming that SAW device 102 has a thin and substantially uniform coating over the whole surface, the diffusion coefficient D of the adsorbed gas molecules is constant along the entire surface of SAW device 102. Due to independent random walking of each molecule, the instantaneous number N(t) of molecules over gas-sensing region 110 will fluctuate with respect to time. Therefore, chemical sensor system 100 will have spontaneous fluctuations of the mean oscillation frequency $f_{osc}$ and the instantaneous value $\Delta f_{osc}(t)$ of the frequency deviation from the frequency of the gas-molecule-free case will be proportional to N(t). The dynamical properties of the fluctuations in N(t) and the induced frequency fluctuations $\Delta f_{osc}(t)$ will be determined by the value of D and the geometry of SAW device 102 and the gas-sensing region 110.

The low-frequency power density spectrum (PSD) S(f) of the AC component of $\Delta f_{osc}(t)$ is described by the diffusion noise theory which, due to the linear coupling between N(t) and $\Delta f_{osc}(t)$, can be directly represented by the equation:

$$S(\omega) = N_{tot} \frac{K \cdot L^2}{D \cdot \Theta^3}[1 - (\cos\Theta + \sin\Theta) \cdot e^{-\Theta}]^2, \qquad \text{(EQ. 1)}$$

where $N_{tot}$ is the total number of gas molecules adsorbed on the surface, K is a constant characterizing the time average $\langle \Delta f_{osc}(t) \rangle_t^2$ of the frequency shift due to a single molecule, L is the length 104c of gas-sensing region 110 of SAW device 102, the angular frequency $\omega = 2 \cdot \pi \cdot f$, and $$\Theta = L \cdot \sqrt{\frac{\omega}{2 \cdot D}} \qquad \text{(EQ. 2)}$$

One feature of EQ. 1 is that the spectrum has two different frequency regimes and, in both regimes, it follows a power-law scaling:

for $\Theta \ll 1$, $S(f) \propto f^{-0.5}$ and for $\Theta \gg 1$, $S(f) \propto f^{-1.5}$. (EQ. 3)

The crossover frequency between the two regimes is given as:

$$\Theta = L \cdot \sqrt{\frac{\omega_c}{2 \cdot D}} \cong 1, \text{ or } f_c \cong \frac{1}{\pi} \cdot \frac{D}{L^2}. \qquad \text{(EQ. 4)}$$

From the theory of diffusive fluctuations, EQ. 1 and 3 are valid even if there is only a single molecule on the surface, $N_{tot}=1$. On the other hand, when the surface contains several gas molecules with different diffusion coefficients, the total spectrum will be the sum of the corresponding spectra of the different gases, represented by:

$$S(f)=N_1 \cdot S(f,D_1)+N_2 \cdot S(f,D_2)+ \ldots N_n \cdot S(f,D_n) \qquad \text{(EQ. 5)}$$

where n is the number of different molecule types.

Chemical sensor system 100 optionally includes a bandpass filter 114, for selecting an oscillatory mode of operation, and amplifier 116 coupled to electrodes 106 and 108.

Also included in chemical sensor system 100 is measurement means for measuring a plurality of frequency fluctuations in oscillatory output signal 117. FIG. 1 shows an example of measurement means as frequency fluctuation counter 118. There are various ways that frequency fluctuation counter 118 may measure these frequency fluctuations. One such method is heterodyning, that is, nonlinearly mixing the oscillatory output signal with a noiseless oscillator signal with a frequency close to the fluctuating signal frequency. At the output of this mixing, the difference of the two frequencies is identified and the relative fluctuations will increase. Zero crossings may then be counted using short term measurements. The zero crossing measurements would give the actual frequency, while the mean of these would result in the mean frequency. The frequency fluctuations, using this heterodyning method, are the difference of the actual and the mean frequencies.

Chemical sensor system 100 also includes PSD means for generating a spectral density signal that is representative of the power spectral density (PSD) of the frequency fluctuations measured in frequency fluctuation counter 118. FIG. 1 shows and example of PSD means as statistical analyzer 120. Statistical analyzer 120 may generate the spectral density signal by way of fast Fourier transformation of the frequency fluctuations.

Included still, in chemical sensor system 100 is diffusion coefficient means for generating a diffusion coefficient signal representative of the diffusion coefficient of the chemical sensor with respect to chemical analyte 112. FIG. 1 shows diffusion coefficient means as statistical analyzer 120. While typical chemical sensor systems only obtain information, such as, total absorbed gas mass, the system and method of fluctuation enhanced gas-sensing using SAW devices is able to analyze the total absorbed-gas mass and the diffusion coefficients of the gas by utilizing EQ. 4. In the case of a chemical analyte with a plurality of molecule types, each diffusion coefficient can be estimated by EQ. 6.

A decision means for generating an analyte output signal 124, that is representative of a characteristic of the chemical analyte 112, is also included in chemical sensor system 100. FIG. 1 shows an example of decision means as pattern recognizer 122. Analyte output signal 124 may represent the identification of the analyte, whether analyte 112 includes a single or multiple different types of molecules. It may also represent the concentration of analyte 112 or the number of different types of molecules in analyte 112. As an example, pattern recognizer 122 may utilize a look-up table, a neural network, or other processing means.

Figure 2:
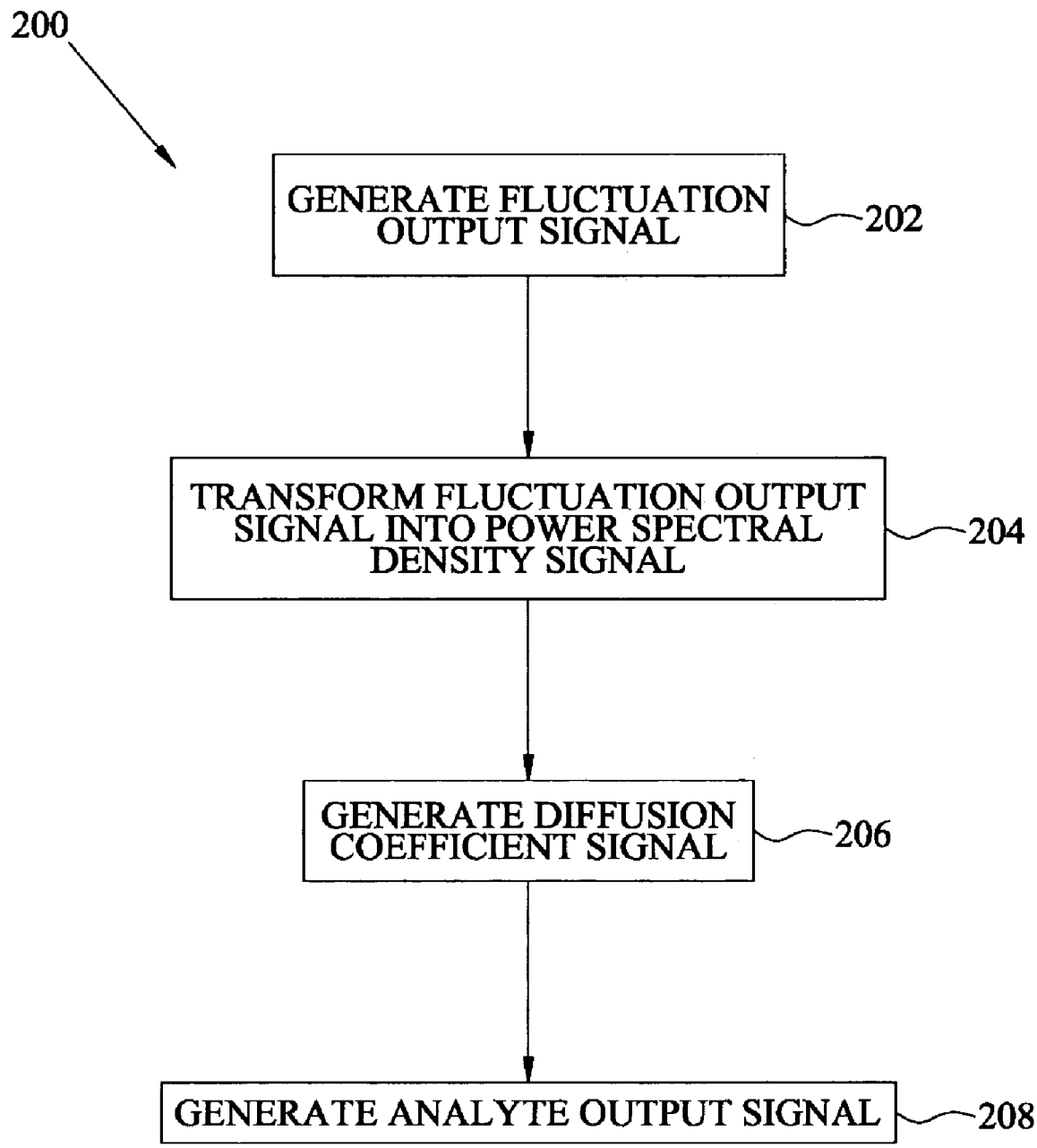
FIG. 2 is a flow-chart of a method in accordance with the system and method of fluctuation enhanced gas-sensing using SAW devices.

FIG. 2 illustrates a method 200 in accordance with the system and method of fluctuation enhanced gas-sensing using SAW devices. Method 200 utilizes statistical analysis of the dynamics of measured frequency fluctuations of a surface acoustic wave (SAW) device that is arranged to produce an oscillatory output signal when exposed to a chemical analyte. Step 202 includes generating a fluctuation output signal in response to a plurality of frequency fluctuations $\Delta f_{osc}$ of the oscillatory output signal. There are various methods that may be implemented for the measurement of the frequency fluctuations. One such method is heterodyning, that is nonlinearly mixing the oscillatory output signal with a noiseless oscillator signal with a frequency close to the fluctuating signal frequency. At the output of this mixing, the difference of the two frequencies is identified and the relative fluctuations will increase. Zero crossings may then be counted using short term measurements. The zero crossing measurements would give the actual frequency, while the mean of these would result in the mean frequency. The frequency fluctuations, using this heterodyning method, are the difference of the actual and the mean frequencies.

Step 204 transforms the fluctuation output signal into a power spectral density signal that is representative of the power spectral density S(f). The S(f) spectrum may be described by EQS. 1, 2, and 5.

Using the measured S(f) implies strongly enhanced selectivity and sensitivity. One of the factors contributing to increased sensitivity of method 200 is the greatly reduced temperature dependence. The drift of the mean oscillation frequency $f_{osc}$ due to temperature variations is typically the dominant limit of the resolution and accuracy of traditional SAW gas-sensing methods. The system and method of fluctuation enhanced gas-sensing using SAW devices is primarily concerned with the power spectral density which is related to the AC component of the frequency fluctuations, thus the temperature dependence, causing a slow DC drift, is significantly reduced. Another important factor contributing to higher sensitivity is the fact that, due to the particular shape of the frequency spectra of diffusion processes, the diffusion noise can be easily distinguished from other sensor noise processes, such as adsorption-desorption, and thermal noise.

The strongly enhanced selectivity also stems from the fact that the power spectral density is a pattern, not a single number. Therefore, the strength and the shape of the S(f) contains information about the absorbed gas molecules.

Step 206 includes generating a diffusion coefficient signal representative of the diffusion coefficient of the chemical sensor with respect to the chemical analyte. While typical gas-sensing methods only obtain information, such as, total absorbed gas mass, the system and method of fluctuation enhanced gas-sensing using SAW devices is able to analyze the total absorbed gas mass and the diffusion coefficients of the gas by utilizing EQS. 1 and/or 4. In the case of a chemical analyte with a plurality of molecule types, each diffusion coefficient can be estimated by EQ. 5.

Lastly, step 208 generates an analyte output signal that is representative of some characteristic of the chemical analyte, if the diffusion coefficient signal corresponds to a characteristic of a known analyte. This characteristic may represent the identification of the analyte that includes a single or multiple different types of molecules. It may also represent the concentration of the analyte or the number of different types of molecules in the analyte. As an example, the characteristic signal may be generated by way of a pattern recognizer, a look-up table, or other processing means.

Figure 3:
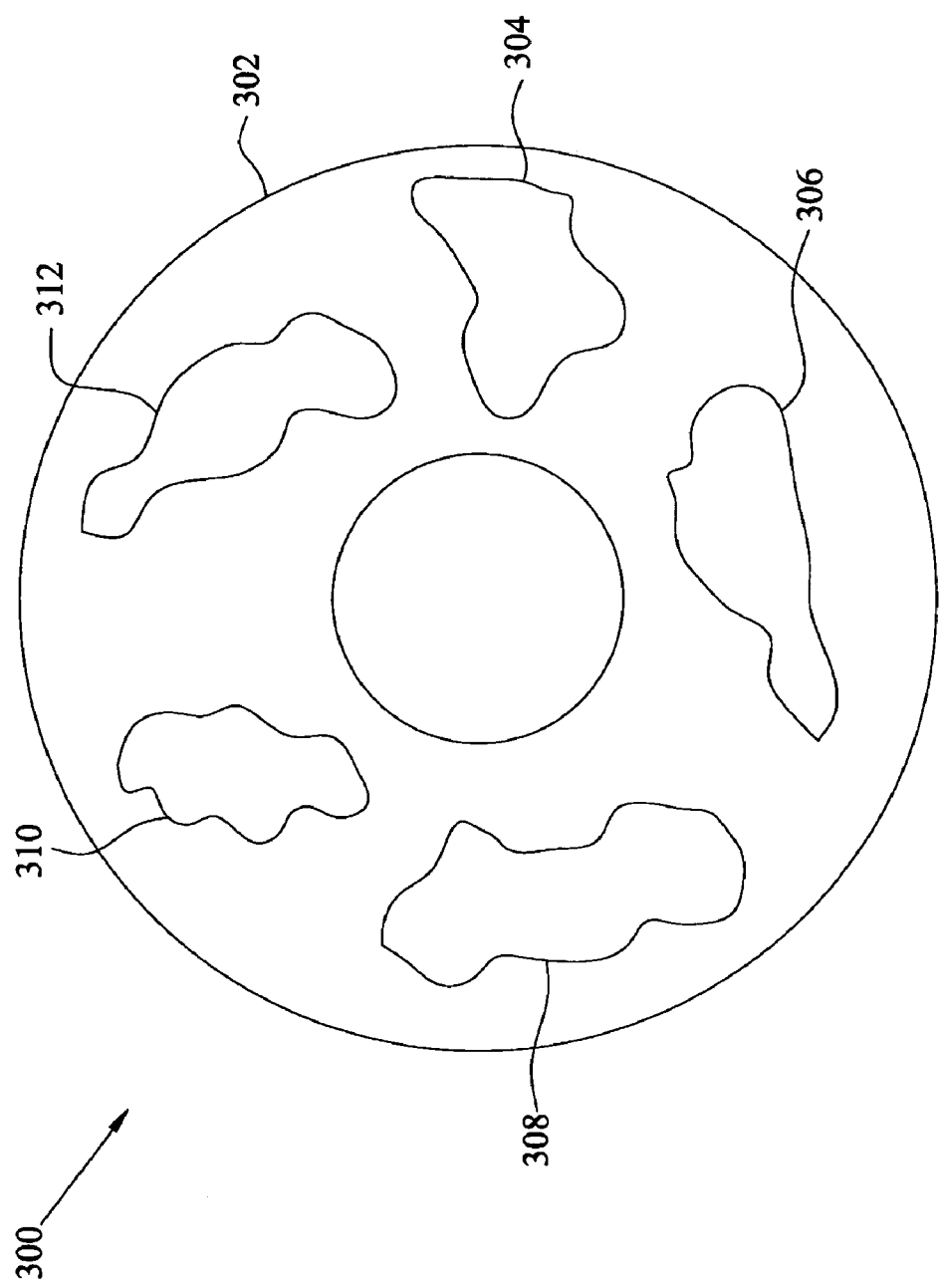
FIG. 3 is a computer program product in accordance with the system and method of fluctuation enhanced gas-sensing using SAW devices.

FIG. 3 illustrates a computer program product (CPP) 300, in accordance with the system and method of fluctuation enhanced gas-sensing using SAW devices. CPP 300 is for use with a chemical sensor system that includes a chemical sensor arranged to produce an oscillatory output signal when exposed to a chemical analyte. CPP 300 includes a machine-readable recording medium 302 and a first, second, and third instruction means, recorded on the recording medium 302.

First instruction means 304 are for directing the chemical sensor system to generate a fluctuation output signal in response to a plurality of frequency fluctuations in the oscillatory output signal generated by the chemical sensor. There are various ways that first instruction means 304 may direct the chemical sensor system to measure these frequency fluctuations. One such method is heterodyning, that is nonlinearly mixing the oscillatory output signal with a noiseless oscillator signal with a frequency close to the fluctuating signal frequency. At the output of this mixing, the difference of the two frequencies is identified and the relative fluctuations will increase. Zero crossings may then be counted using short term measurements. The zero crossing measurements would give the actual frequency, while the mean of these would result in the mean frequency. The frequency fluctuations, using this heterodyning method, are the difference of the actual and the mean frequencies.

Second instruction means 306 are for directing the chemical sensor system to generate a power spectral density signal that is representative of the power spectral density of the frequency fluctuations in the oscillatory output signal. By way of example, second instruction means 306 may direct the chemical sensor system to generate the power spectral density signal through fast Fourier transformation (FFT) of the frequency fluctuations.

Third instruction means 308 are for directing the chemical sensor system to generate a diffusion coefficient signal representative of the diffusion coefficient of the chemical sensor with respect to the chemical analyte. While typical chemical sensor systems only obtain information, such as, total absorbed gas mass, the system and method of fluctuation enhanced gas-sensing using SAW devices is able to analyze the total absorbed gas mass and the diffusion coefficients of the gas by utilizing EQS. 1 and/or 4. In the case of a chemical analyte with a plurality of molecule types, each diffusion coefficient can be estimated by EQ. 5.

Fourth instruction means 310 are for directing the chemical sensor system to generate an analyte output signal that identifies a characteristic of the chemical analyte, if the diffusion coefficient signal corresponds to a characteristic of a known analyte. This analyte output signal may represent the identification of the analyte that includes a single or multiple different types of molecules. It may also represent the concentration of the analyte or the number of different types of molecules in the analyte. As an example, fourth instruction means 310 may utilize a look-up table, a neural network, or other processing means.

Optionally included in CPP 300 is a fifth instruction means, recorded on the recording medium 302 for directing the chemical sensor system to correlate patterns in the power spectral density to a characteristic of known chemicals.

Figure 4:
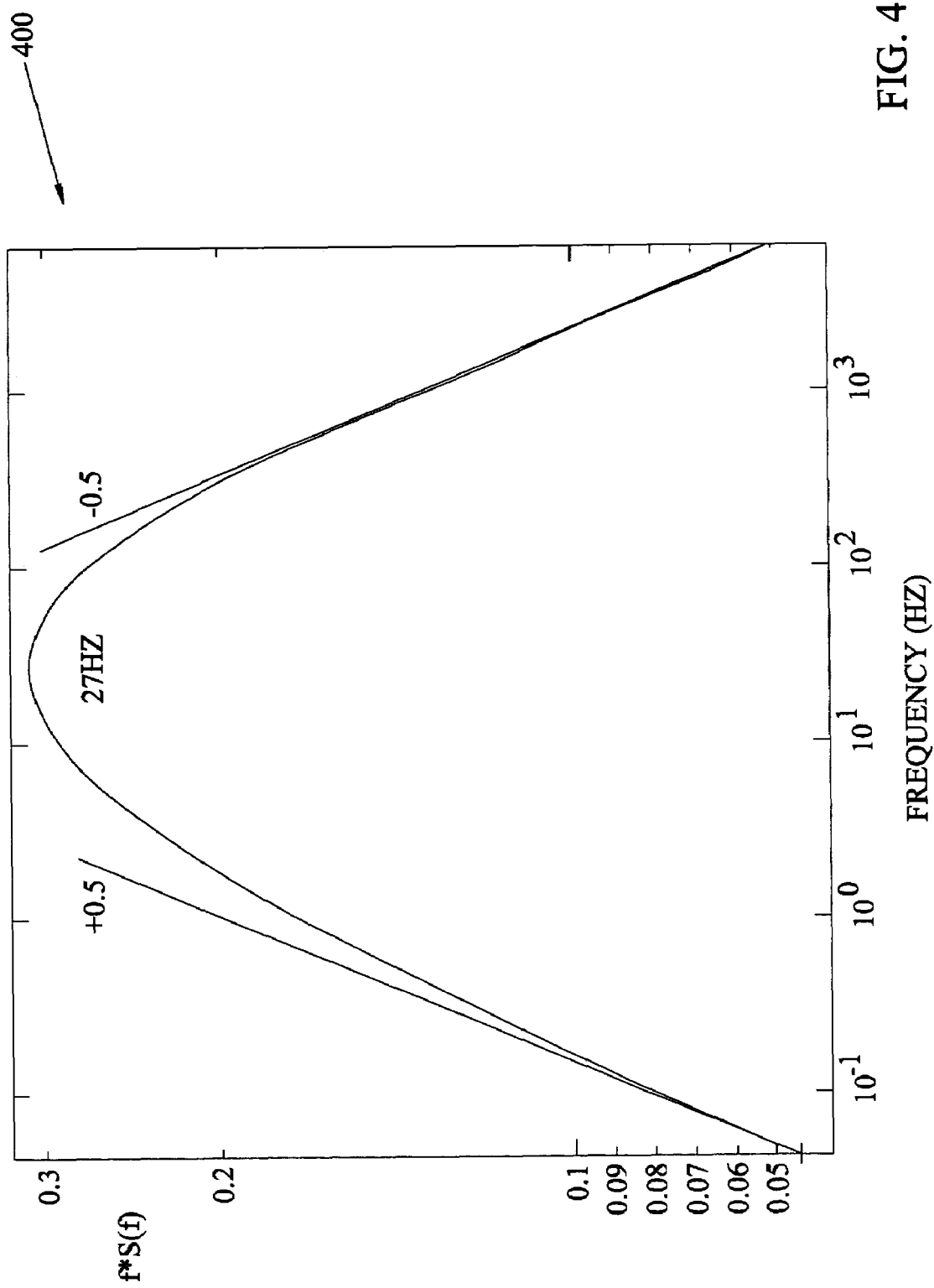
FIG. 4 is a view showing the f*S(f) pattern for a SAW device measuring a single chemical agent in accordance with the system and method of fluctuation enhanced gas-sensing using SAW devices.

FIG. 4 illustrates the f*S(f) pattern 400 of a representative embodiment of the system and method of fluctuation enhanced gas-sensing using SAW devices.

The f*S(f) pattern 400 shown in FIG. 4 is the case of a SAW device sensing an analyte with a single agent with activation energy E=0.1 eV. The SAW device includes the following constraints: L=0.1 mm, d=0.3 nm, T=400 K, and $f_0=2*10^{14}$. As shown in FIG. 5 the crossover frequency is 27 Hz. From the measurement of this crossover frequency, the diffusion coefficient D of the analyte can be determined so it can be identified. Note that the obtained curve, which is plotted on a log-log scale, converged to a slope of 0.5 in the low frequency limit and −0.5 in the high frequency limit.

The f*S(f) pattern 400 shown in FIG. 4 is the case of a SAW device sensing an analyte with two different agents with activation energies $E_1=0.1$ eV and $E_2=0.245$ eV. The SAW device, again, includes the following constraints: L=0.1 mm, d=0.3 nm, T=400 K, and $f_0=2*10^{14}$. The two dashed curves show the independent spectral contribution of the different agents. The measured (solid) curve is the sum of these two curves. By using EQ. 5 and the known shape for a single agent, the dashed curves can be reconstructed by two-component analysis from the measured sum and the agents can be identified. After calibrating the SAW device for different gases and gas concentrations, the dashed curves can be used for quantitative analysis of gas mixtures.

We claim:

1. A method of analyzing a chemical analyte, said method comprising the steps of:

generating a fluctuation output signal in response to a plurality of frequency fluctuations in an oscillatory output signal of a SAW device;

transforming said fluctuation output signal into a power spectral density (PSD) signal, representative of the power spectral density of said frequency fluctuations;

generating a diffusion coefficient signal in response to said power spectral density signal, representative of a diffusion coefficient of said analyte; and generating an analyte output signal that identifies a characteristic of said analyte if said diffusion coefficient signal corresponds to a characteristic of a known analyte.

2. The method as in claim 1, wherein said analyte output signal represents a characteristic of said analyte selected from the group consisting of: identification and concentration.

3. The method as in claim 1, wherein said analyte output signal is representative of a number of molecules for each of a plurality of molecule types in said chemical analyte and is responsive to the function $S(f)=N_1S(f,D_1)+N_2S(f,D_2)+ \ldots N_nS(f,D_n)$, where S(f) is the total power spectral density, n is the number of molecule types, Nn is the number of molecules of molecule type n, Dn is the diffusion coefficient of said molecule type n, and S(f,Dn) is the power spectral density determined by each said diffusion coefficient.

4. The method as in claim 1, wherein said generating a diffusion coefficient signal step further includes the step of comparing said power spectral density signal to a calculated power spectral density $S(\omega)$, represented substantially by the equation:

$$S(\omega) = N_{tot} \cdot \frac{K \cdot L^2}{D \cdot \Theta^3} [1 - (\cos\Theta + \sin\Theta) \cdot e^{-\Theta}]^2,$$

where $N_{tot}$ is the total number of gas molecules, K is a constant characterizing a time average of a frequency shift due to a single molecule, L is a length of a gas-sensing region of said SAW device, ω is the angular frequency, D is said diffusion coefficient, and $$\Theta = L \cdot \sqrt{\frac{\omega}{2 \cdot D}}.$$

5. A chemical sensor system comprising:

a chemical sensor that produces an oscillatory output signal when exposed to a chemical analyte;

measurement means for measuring a plurality of frequency fluctuations of said oscillatory output signal;

PSD means, coupled to said measurement means, for generating a power spectral density signal representative of the power spectral density (PSD) of said plurality of frequency fluctuations;

diffusion coefficient means, coupled to said PSD means, for generating a diffusion coefficient signal representative of the diffusion coefficient of said chemical analyte; and decision means, coupled to said diffusion coefficient means, for generating an analyte output signal that identifies a characteristic of said chemical analyte if said diffusion coefficient signal corresponds to a characteristic of a known analyte.

6. The chemical sensor system as in claim 5, wherein said analyte output signal represents a characteristic of said analyte selected from the group consisting of:

identification and concentration.

7. The chemical sensor system as in claim 5, wherein said chemical sensor is a Surface Acoustic Wave (SAW) device having a total length $l_{tot}$.

8. The chemical sensor system as in claim 7, wherein said SAW device comprises:
  a chemical sensing region; and
  first and second electrode pairs coupled to opposing ends of said chemical sensing region.

9. The chemical sensor system as in claim 5, wherein said chemical sensor further comprises a bandpass filter for selecting a single oscillatory mode.

10. The chemical sensor system as in claim 5, wherein said measurement means comprises a frequency fluctuation counter.

11. The chemical sensor system as in claim 5, wherein said PSD means comprises a fast Fourier transformation spectrum analyzer.

12. The chemical sensor system as in claim 5, wherein said decision means comprises a pattern recognizer for correlating patterns in said power spectral density to a characteristic of known chemicals.

13. A computer program product for use with an chemical sensor system including a chemical sensor arranged to produce an oscillatory output signal when exposed to a chemical analyte, said computer program product comprising:
  a machine-readable recording medium;
  a first instruction means, recorded on said recording medium, for directing said chemical sensor system to generate a fluctuation output signal in response to a plurality of frequency fluctuations in said oscillatory output signal;
  a second instruction means, recorded on said recording medium, for directing said chemical sensor system to generate a power spectral density signal representative of the power spectral density (PSD) of said plurality of frequency fluctuations in response to said fluctuation output signal;
  a third instruction means, recorded on said recording medium, for directing said chemical sensor system to generate a diffusion coefficient signal representative of the diffusion coefficient of said chemical analyte, responsive to said power spectral density signal; and
  a fourth instruction means, recorded on said recording medium, for directing said chemical sensor system to generate an analyte output signal that identifies a characteristic of said chemical analyte if said diffusion coefficient signal corresponds to a characteristic of a known analyte.

14. The computer program product as in claim 13, wherein said analyte output signal is representative of a characteristic of said analyte selected from the group consisting of: identification and concentration.

15. The computer program product as in claim 13, wherein said chemical sensor is a Surface Acoustic Wave (SAW) device.

16. The computer program product as in claim 13, further comprising:
  a fifth instruction means, recorded on said recording medium, for directing said chemical sensor system to correlate patterns in said power spectral density to a characteristic of known chemicals.

17. A method of analyzing a chemical analyte, said method comprising the steps of:
  generating a surface acoustic wave across a surface of a structure;
  transducing said surface acoustic wave into a oscillatory output signal;
  generating a fluctuation output signal in response to a plurality frequency fluctuations in said oscillatory output signal;
  transforming said fluctuation output signal into a power spectral density (PSD) signal, representative of the power spectral density of said frequency fluctuations;
  generating a diffusion coefficient signal in response to said power spectral density signal, representative of a diffusion coefficient of said analyte; and
  generating an analyte output signal that identifies a characteristic of said analyte if said diffusion coefficient signal corresponds to a characteristic of a known analyte.

18. The method as in claim 17, wherein said analyte output signal represents a characteristic of said analyte selected from the group consisting of: identification and concentration.

19. The method as in claim 17, wherein said analyte output signal is representative of a number of molecules for each of a plurality of molecule types in said chemical analyte and is responsive to the function $S(f)=N_1 S(f,D_1)+N_2 S(f, D_2)+ \ldots N_n S(f,D_n)$, where $S(f)$ is the total power spectral density, n is the number of molecule types, Nn is the number of molecules of molecule type n, D is the diffusion coefficient of said SAW device with respect to molecule type n, and $S(f,Dn)$ is the power spectral density determined by each said diffusion coefficient.

20. The method as in claim 17, wherein said generating a diffusion coefficient signal step further includes the step of comparing said power spectral density signal to a calculated power spectral density $S(\omega)$, represented substantially by the equation:

$$S(\omega) = N_{tot} \cdot \frac{K \cdot L^2}{D \cdot \Theta^3}[1 - (\cos\Theta + \sin\Theta) \cdot e^{-\Theta}]^2,$$

where $N_{tot}$ is the total number of gas molecules, K is a constant characterizing a time average of a frequency shift due to a single molecule, L is a length of a gas-sensing region of said SAW device, $\omega$ is the angular frequency, D is said diffusion coefficient, and $$\Theta = L \cdot \sqrt{\frac{\omega}{2 \cdot D}}.$$

* * * * *